United States Patent
Savage

(10) Patent No.: US 10,252,079 B2
(45) Date of Patent: Apr. 9, 2019

(54) HAND-HELD LIGHT THERAPY APPARATUS

(75) Inventor: Kent W. Savage, American Fork, UT (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 923 days.

(21) Appl. No.: 10/692,893

(22) Filed: Oct. 24, 2003

(65) Prior Publication Data
US 2004/0249423 A1 Dec. 9, 2004

Related U.S. Application Data

(60) Provisional application No. 60/476,574, filed on Jun. 6, 2003.

(51) Int. Cl.
*A61N 5/06* (2006.01)
*A61M 21/00* (2006.01)

(52) U.S. Cl.
CPC ........... *A61N 5/0618* (2013.01); *A61M 21/00* (2013.01); *A61M 2021/0044* (2013.01); *A61M 2205/8206* (2013.01); *A61M 2209/084* (2013.01); *A61N 5/0616* (2013.01); *A61N 2005/0627* (2013.01); *A61N 2005/0644* (2013.01); *A61N 2005/0652* (2013.01); *A61N 2005/0655* (2013.01)

(58) Field of Classification Search
CPC ............... A61N 5/0618; A61N 5/0616; A61N 2005/0627; A61N 2005/0644; A61N 2005/0652; A61N 2005/0655; A61M 21/00; A61M 2021/0044; A61M 2205/8206; A61M 2209/084

USPC ............... 362/103, 104, 194, 184, 195, 209, 362/219–225, 257, 266, 276; 361/681; 606/10–13; 607/88, 89
See application file for complete search history.

(56) References Cited

U.S. PATENT DOCUMENTS

| | | | | |
|---|---|---|---|---|
| 4,545,658 A | * | 10/1985 | Weiss | 351/222 |
| 5,149,184 A | * | 9/1992 | Hughes | A61N 5/0618 362/1 |
| 5,447,528 A | | 9/1995 | Geraldo | |
| 5,467,258 A | * | 11/1995 | Bamber et al. | 362/184 |
| 5,493,183 A | * | 2/1996 | Kimball | G09G 3/3406 315/156 |

(Continued)

FOREIGN PATENT DOCUMENTS

| EP | 0228288 | * | 7/1987 |
|---|---|---|---|
| EP | 1134491 A2 | | 9/2001 |

(Continued)

OTHER PUBLICATIONS

HP Jornada 700 Series Handheld PC User's Guide; pp. 129, 136; 2001.*

(Continued)

*Primary Examiner* — David Shay

(57) ABSTRACT

A light therapy apparatus is provided for delivering ocular light to a subject to treat disorders that are responsive to ocular light therapy, including a power supply and a hand-held light output device. The light output device includes a plurality of light sources powered by the power supply. A method of light therapy is provided, wherein ocular light is administered to a subject to treat disorders that are responsive to ocular light therapy. The method includes delivering the light to the eyes of a subject by a hand-held light source operated by a power supply.

31 Claims, 5 Drawing Sheets

(56) References Cited

U.S. PATENT DOCUMENTS

| | | | |
|---|---|---|---|
| 5,503,637 A * | 4/1996 | Kyricos et al. | 607/88 |
| 5,589,741 A * | 12/1996 | Terman et al. | 315/360 |
| 5,698,866 A * | 12/1997 | Doiron | A61N 5/062 |
| | | | 604/20 |
| 5,880,946 A * | 3/1999 | Biegel | 363/75 |
| 6,053,938 A | 4/2000 | Koyama et al. | |
| 6,111,980 A * | 8/2000 | Sano et al. | 382/167 |
| 6,135,117 A | 10/2000 | Campbell et al. | |
| 6,135,620 A * | 10/2000 | Marsh | 362/377 |
| 6,317,347 B1 * | 11/2001 | Weng | H02M 7/5381 |
| | | | 315/219 |
| 6,350,275 B1 | 2/2002 | Vreman et al. | |
| 6,381,124 B1 * | 4/2002 | Whitcher et al. | 361/681 |
| 6,454,789 B1 | 9/2002 | Chen | |
| 6,488,698 B1 | 12/2002 | Hyman | |
| 6,596,571 B2 * | 7/2003 | Arao et al. | 438/163 |
| 6,612,713 B1 * | 9/2003 | Kuelbs | 362/102 |
| 6,831,689 B2 * | 12/2004 | Yadid-Pecht | 348/297 |
| 6,875,225 B1 * | 4/2005 | Pederson et al. | 607/88 |
| 7,057,886 B2 * | 6/2006 | Yano et al. | 361/681 |
| 2001/0056293 A1 | 12/2001 | Brainard | |

FOREIGN PATENT DOCUMENTS

| | | |
|---|---|---|
| EP | 1285676 A2 | 2/2003 |
| WO | 198908475 | 9/1989 |
| WO | 2003040808 A2 | 5/2003 |

OTHER PUBLICATIONS

Chen, "A Cold Cathode Fluorescent Lamp (CCFL) Controller Used in Magnetic Transformer Application," <http://www.chipcenter.com/analog/c070.htm>, accessed Jun. 6, 2003.

* cited by examiner

HAND-HELD LIGHT THERAPY APPARATUS

RELATED APPLICATION

This application claims the priority of provisional application No. 60/476,574 filed Jun. 6, 2003.

FIELD

This application relates to light therapy apparatus and methods. More particularly, this application concerns apparatus and methods for delivering light to a subject's eyes to provide circadian rhythm adjustments, and treat seasonal affective disorder and other disorders or problems that can be effectively treated with light therapy.

BACKGROUND

Light therapy systems have been widely used for some time to treat circadian rhythm disorders, seasonal affective disorder and other such problems by delivering light through the eyes of a subject. One problem has been the need to provide the necessary light intensity and color spectrum, similar to daylight. In many cases fluorescent lights are used because they tend to provide an effective spectrum of light and are longer lasting than incandescent lamps. However, the high intensities of light needed for such treatments required relatively large-sized lamps and other components. Thus, many commercial light therapy units have been large, bulky and cumbersome.

In the last decade, advances in ballast and fluorescent light technology have allowed some companies to produce smaller, lighter-weight light therapy units. An example is shown in U.S. Pat. No. 6,488,698 (Hyman). Such units, though smaller and less cumbersome than previously mentioned designs, are usually too large to be hand-held. Further, the Hyman device has no display or other means to convey information.

Some products have been made portable by developing wearable devices which bring the light source close enough to the subject's eyes to achieve the effective high-intensity lux output. These units typically incorporate smaller, less intense lamps that can be battery powered. Examples are shown in U.S. Pat. No. 5,447,528 (Geraldo); U.S. Pat. No. 6,350,275 (Vreman et al.); and U.S. Pat. No. 6,053,936 (Koyama et al.).

Such devices tend to flood the user's field of vision with light. This makes it difficult for the user to look past the bright light source to more dimly lit surfaces to accomplish daily tasks. This arrangement can cause eyestrain, headache and other discomforts.

Another approach involves using LEDs to try to make portable devices. However, prior art LED ocular devices tend to be harsh to the eyes and create retinal after imaging. Prior art LED devices are of limited portability because of power consumption that requires access to an external power outlet or relatively large cumbersome batteries, rather than using a portable or built-in battery pack.

Some products have addressed the portability and eyestrain problems by developing devices worn against the skin. These non-ocular approaches radiate light energy through the skin to the blood stream. Examples are shown in U.S. Pat. No. 6,135,117 (Campbell et al.) and U.S. Pat. No. 6,350,275 (Vreman et al.). These units have not yet been proven effective in large clinical trials.

SUMMARY

In one implementation, a light therapy apparatus is provided for delivering ocular light to a subject to treat disorders that are responsive to ocular light therapy. The apparatus includes a power supply and a hand-held light output device. The hand-held light output device includes a plurality of light sources powered by the power supply.

In another implementation, a method of light therapy is provided, wherein ocular light is administered to a subject to treat disorders that are responsive to ocular light therapy. The method includes delivering the light to the eyes of a subject by a hand-held light output device operated by a power supply.

DETAILED DESCRIPTION

The light therapy device of the present disclosure delivers a full spectrum of light to the subject, while being fully portable and substantially avoiding eyestrain. In addition, the present light therapy device provides a process to make the necessary circadian rhythm adjustments in the subject's body suffering from jet lag by selectively applying the light based on the direction and extent of travel. The light therapy device of the present disclosure is also effective in treating other light-related problems, such as other circadian rhythm problems, seasonal affective disorders, some forms of depression, sleep disorders, and shift-work disorders, post- and ante-partum depression, pre-menstral syndrome, late luteal phase dysphoric disorder (LLPDD), bulimia and eating disorders, and chronic fatigue.

The ocular light therapy devices of the present disclosure are not only portable, they are hand-held devices. As used here, the term "portable" shall be broadly understood to mean being capable of being easily transferred to different locations. Thus, typically a unit the size of a briefcase or smaller might be termed to be portable, even though it must be connected to a wall outlet power source at each location. There is also a category of devices referred to as "wearable," distinguished by being able to wear the device on the body, usually in close proximity to the eyes, such as on a visor. Wearable devices are further characterized by having a relatively low output, so that they are normally placed just a few inches from the eyes in order to be effective. As used here, the term "hand-held" refers to portable devices that are not wearable, that are capable of being powered by portable batteries, and that are relatively small—about 3 to 4 pounds or less and having dimensions in each direction of less than 10 inches.

Figure 1:
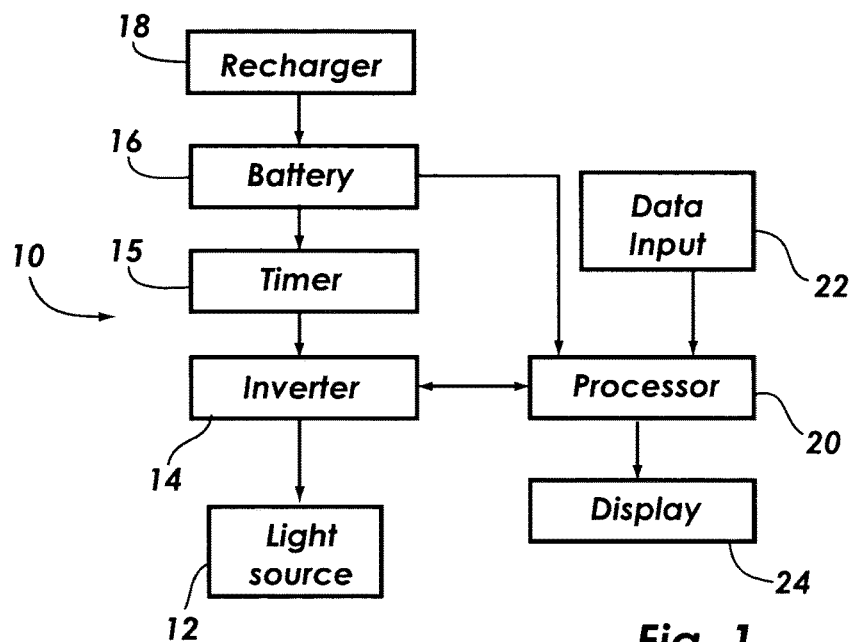
FIG. 1 is a schematic diagram generalizing the light device of the present disclosure.

FIG. 1 is a generalized schematic diagram showing the elements of the hand-held light therapy device 10 according to the present disclosure. A light source 12 is driven by an inverter 14 which in turn is powered by a battery 16 or can also be powered by an AC adaptor connected to a standard power outlet. Battery 16 may be rechargeable and connected to a recharger 18 that in turn may connect to a conventional AC power outlet. Battery 16 also supplies power to a processor 20 that has two-way control and data communication with inverter 14. Data is provided by data input device 22. Processor 20 also provides a data and message display 24 and may also include integral timing functions. A timer 15 may also be connected between the battery 16 and the inverter 14, so that the device 10 may be manually actuated for a selected period of time.

It should be understood that the some elements of the system shown in FIG. 1 are optional to the present implementation. The main elements include the battery power source 16 having an on-off switch, the battery 16 being coupled to the inverter 14 that activates the light source 12 providing therapeutic light. The other elements shown, such as the timer 15, processor 20, data input 22 and display 24 may be added, as desired.

Figure 2:
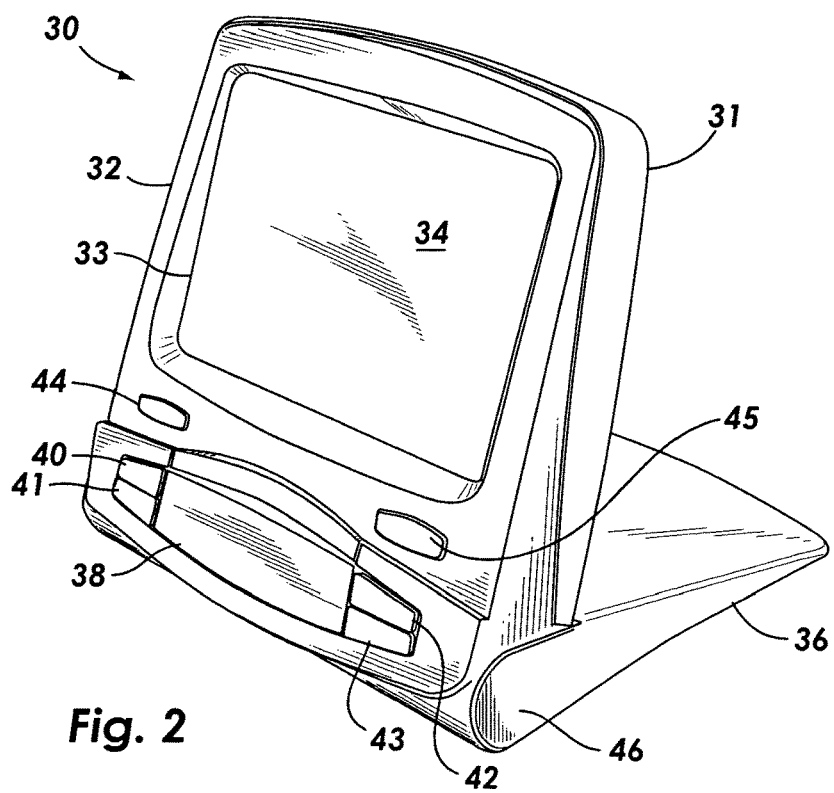
FIG. 2 is an open-cover perspective view of one implementation of the light device of the present disclosure.
Figure 3:
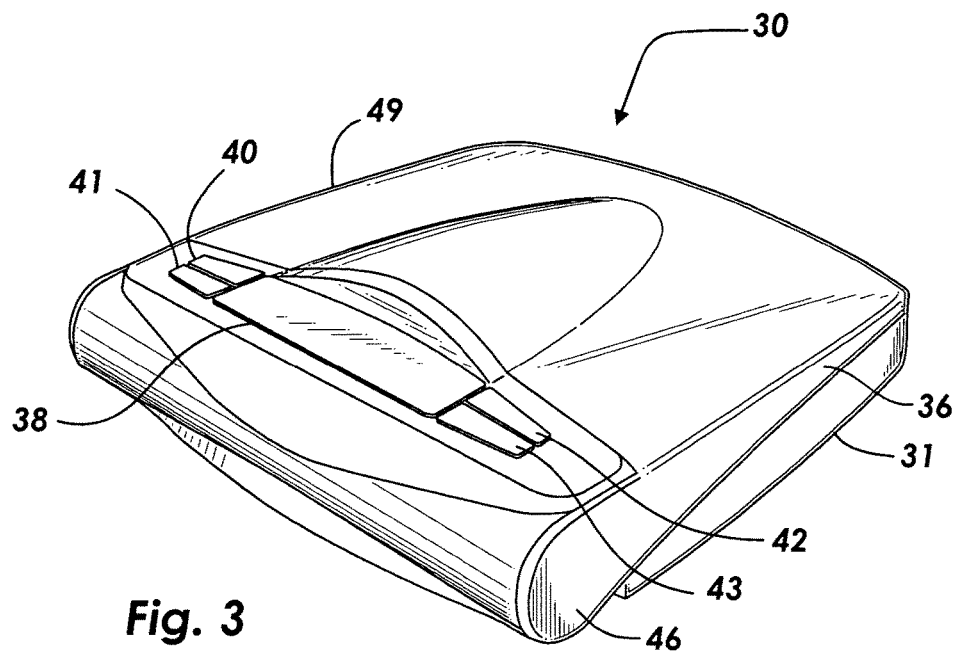
FIG. 3 is a closed-cover perspective view of the implementation of FIG. 1.

FIGS. 2 and 3, show one implementation of a hand-held light therapy unit 30. Unit 30 is a battery powered, ocular, hand-held therapy device that incorporates a unique type of fluorescent light source referred to as cold cathode fluorescent lamps, referred to as CCFL. CCFL tubes are usually low pressure lamps, possibly using mercury vapor, and having a very small diameter (for example, 2 to 3 mm) and short length (for example, 50 to 700 mm).

CCFL tubes have been used to provide background lighting for laptop computers and to provide light for scanning and copying, because they provide an even distribution of light and can produce full-spectrum coloring and/or single-out specific wavelengths. See, e.g., "A Cold Cathode Fluorescent Lamp (CCFL) Controller Used in Magnetic Transformer Application," by Weiyun (Sophie) Chen, an article located on the internet at a web page having the Internet address of chipcenter.com/analog/c070.htm (accessed Jun. 6, 2003). Another application of CCFL tubes is shown in U.S. Pat. No. 6,454,789 (Chen) where light is provided via fiber optics to treat tumors within a patient's body.

CCFL tubes are small and portable, and provide high efficiency in light output. They are also effective in providing a substantially full spectrum of light or an emphasis on a specific wavelength or range of wavelengths, thereby facilitating effective therapy. Unit 30 may be relatively small. For example, the unit may be about six inches in length by five inches wide by two inches thick. The device typically provides intensities of 2,500 lux, 5,000 lux and 10,000 lux, which are adequate for most light therapy applications. Consequently, it is readily portable and may be used in travel, at the bedside and in many situations where larger units would be too intrusive.

Referring to FIG. 2, a light therapy unit 30 according to one implementation of the present disclosure is shown in an open position. A generally rectangular case 32 includes a recess 33 having a lens 34 therein. A light source 50 (shown in FIG. 4) is disposed in the back portion 31 of case 32 behind the lens 34. Case 32 rests in an upright position on a base 36, held in place by a protrusion on the base (not shown). Below lens 34 is a display 38 for depicting messages and data during use. On either side of display 38 are data input buttons 40-43 for providing data to the unit 30, as will be discussed in detail hereafter. Between the display 38 and the lens 34 are two buttons 44 and 45, for the on/off switch and other main menu selections.

When the unit 30 is not in use, it is placed in the closed position, as shown in FIG. 3. Base 36 is hinged at end 46 so that it rotates approximately 270 degrees to form a cover 49 protecting lens 34 and the light sources behind it, as well as buttons 44 and 45, shown in FIG. 2. With base 36 out of the way, unit 30 is configured to sit flat on back portion 31 as shown, with display 38 and buttons 40-43 on the top of the unit. This closed position not only protects the lens 34 and the light source 50, but also provides a slim, compact unit that is hand-held and can easily be stored or transported.

Figure 4:
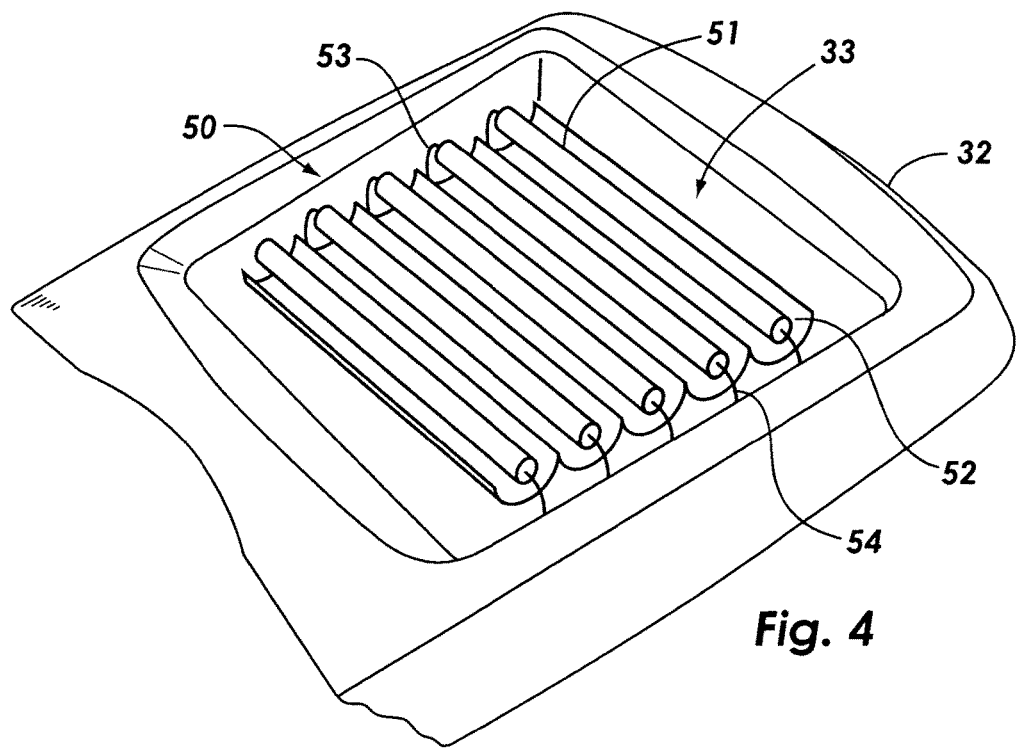
FIG. 4 is a partial perspective view of the implementation of FIG. 1.

Looking at FIG. 4, a light source 50 is shown. Six CCFL tubes 51 are placed in a generally parallel position relative to each other in recess 33 of case 32. A generally parabolic reflector 52 is positioned behind each of tubes 51 for directing light toward the front of the unit 30. Each tube 51 has electrical connections 53 and 54 extending from each end to connect to an inverter 60 (shown in FIG. 5).

Figure 5:
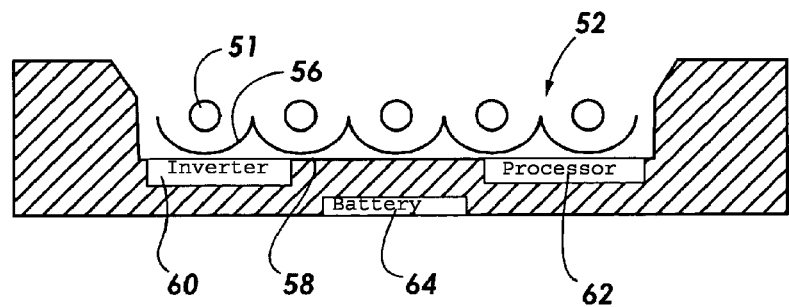
FIG. 5 is a partial side view of the implementation of FIG. 4.

FIG. 5 shows the light source 50 from a side view. Each of tubes 51 lies within the focal point of a parabolic portion 56 of reflector 52. Reflector 52 rests on a circuit board 58 to which the tubes 51 and reflector 52 are attached. On the underside of circuit board 58 is an inverter 60 and processor 62, corresponding to inverter 14 and processor 20 in FIG. 1. Battery 64 is disposed just inside of case 32.

Figure 6:
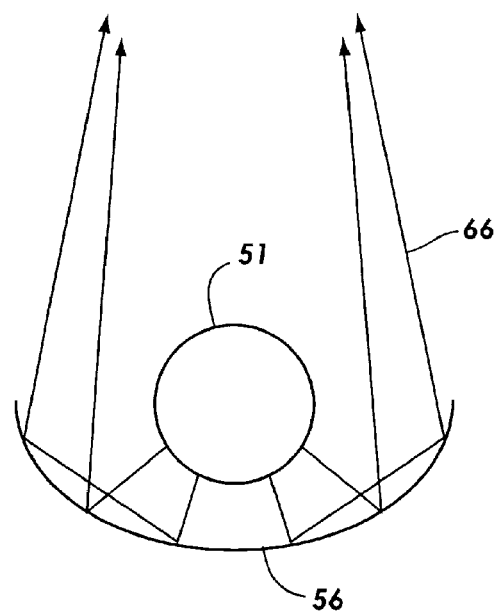
FIG. 6 is a close-up partial side view of the view shown in FIG. 5.

As shown in FIG. 6, each tube 51 is disposed at the focal point of a respective parabolic portion 56 so that the rays of light 66 reflecting from the parabolic portion are directed out the front of unit 30 and towards the user to provide maximum reflectivity of the generated light.

The light therapy unit 30 may use multiple cold cathode fluorescent technology for the treatment of light related problems, such as circadian rhythm problems and mood and sleep disorders. The light therapy unit 30 described herein may provide long life (about 20,000 hours), substantially full-spectrum color and high output over specific wavelengths, such as blue or green light wavelengths, while minimizing the presence of ultraviolet wavelengths. The device also may have a high CRI (Color Rendition Index), which is a measure of the trueness of color reflected when the light is exposed to a given color. In addition, the CCFL tubes of the present device may include one lead on each end. They may have a very small diameter, about the size of a plastic ink cylinder of a small writing pen.

The inverter 60 of the present device may include a unit with the ability to dim down and ramp up the light output from the light source. One embodiment includes a dimming/ramping function built into the inverter. The dimming function enables a dusk simulation to aid in falling asleep, and the ramping function allows for natural waking.

Contrary to most uses of CCFL tubes, the high-intensity inverter 60 of the present device is designed to run multiple CCFLs. This allows for fewer electronic components and thus lighter weight and smaller overall size of the unit.

The efficiencies of the CCFL technology allow the unit 30 to be battery-powered. The device is designed to run on a multi-current wall transformer 120 volts or 240 volts, plus or minus 20%. The unit 30 may also contain rechargeable batteries with a capacity to allow multiple therapy sessions.

The parabolic reflector unit 56 may be made of aluminum or other material which is 90% reflective or greater. The reflector material is bent in a parabolic shape that insures that the light emitted from the tubes 51 is reflected forward to the user.

The present device employs a very thin (1/16 inch) lens 34 which may be textured and made of clear acrylic. The diffraction of the light passing through the texture of the lens softens the high-intensity light and allows a more uniform treatment field. The acrylic properties of the lens 34 filter the ultraviolet rays so that the lens 34 will not yellow over time.

The CCFL tubes 51 may have a diameter of 2.2 mm and a length of 140 mm. The lamp voltage may be 340 volts with a wattage of 1.7 watts at 5 mA rms and a tube current of 6 milliamps. The inverter 60 may have a strike voltage of 730 volts and a sustain voltage in the range of 325-450 volts. The inverter frequency can be 60 kilohertz. Ramping and dimming may be done through pulse width modulation (PWM) of the CCLF current. This PWM frequency is superimposed on the 60 khz current frequency, and averages 120 hz. By varying the duty cycle, the CCFL's cam be dimmed by turning the current on and off at a sufficient rate to prevent the excitation of the lamp to decay, yet reduce the emissions.

Figure 7:
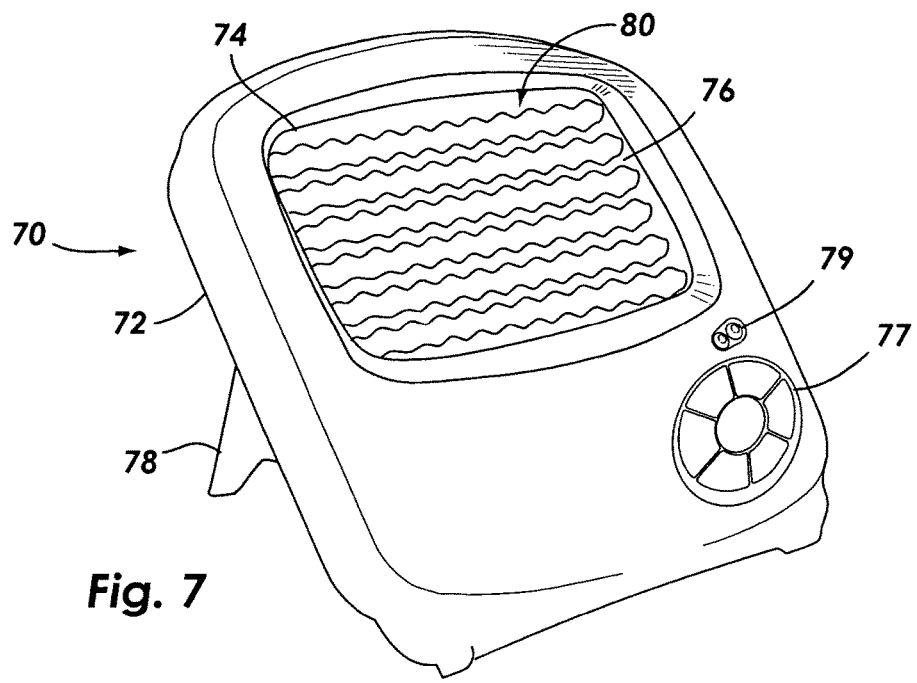
FIG. 7 is a perspective view of another implementation of the light device of the present disclosure.
Figure 8:
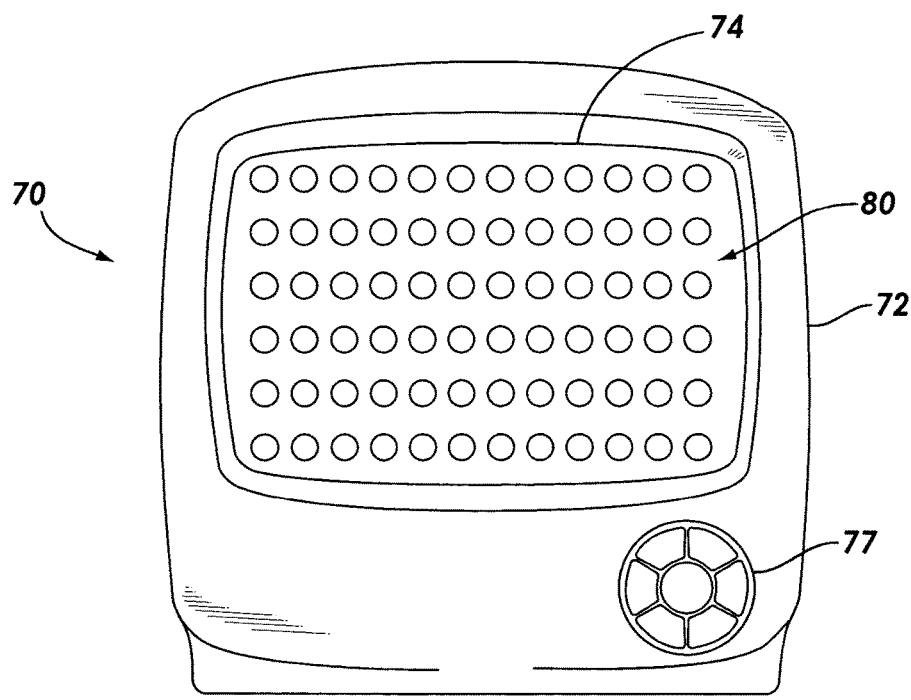
FIG. 8 is a plan view of the implementation of FIG. 7.

Referring now to FIGS. 7 and 8, another implementation of the present disclosure is shown in the form of a hand-held light therapy unit 70. Unit 70 is an ocular therapy hand-held device that incorporates a light source using a matrix of LEDs 80, and capable of being battery-powered. Unit 70 comprises a casing 72 having a recess 74 for the matrix 80. A lens 76 is positioned in front of the matrix 80 to protect the source and to diffuse the intensity of the light. The light therapy unit 70 described herein may provide long life, substantially full-spectrum color and/or high output over specific wavelengths, such as blue or green light wavelengths, while minimizing the presence of ultraviolet wavelengths. The device also may have a high CRI (Color Rendition Index), which is a measure of the trueness of color reflected when the light is exposed to a given color. A fold-out stand 78 is position at the back of casing 72 to support unit 70 in an upright position. A circular button unit 77 provides buttons to activate the unit 70 and to operate a timer in the unit. Other buttons may be used for various functions, including activating various soothing sounds to accompany light therapy. A set of one or more lights 79 indicates whether the unit 70 is turned on and whether other functions have been activated.

FIG. 8 shows a plan view of hand-held unit 70 with the lens 76 removed to more clearly show the matrix of LEDs 80. Matrix 80 is made up of 72 LEDs arranged in 6 rows and 12 columns. The LEDs may be 5 mm oval LEDs emitting a selected spectrum of visible light. The hand-held unit may be about 6 inches tall, 6 inches wide, and about 1 inch deep, weighing about 8.4 ounces. The light emission from light source 80 may fall in an effective range of 1,000 lux to 2,000 lux at 6 to 12 inches.

It should be understood that the light therapy unit 30 shown in FIGS. 2-6 and the light therapy unit 70 shown in FIGS. 7 and 8 are specific implementations of the generalized light therapy device 10 shown in FIG. 1. For both implementations shown herein, the light therapy devices are made to be powered by a conventional internal or external battery pack. However, they may also be powered by an AC adaptor using standard wall-socket power.

The processor 20, shown in FIG. 1, may include an atomic clock and a jet-lag calculator to help travelers to change their sleep patterns and circadian rhythms when they travel. The atomic clock may monitor time across time zones and display the time at the current location. The jet-lag calculator may advise a user, when traveling, about the times to use the device and the amount of light usage. The data may also advise the user when to avoid outdoor light.

Figure 9:
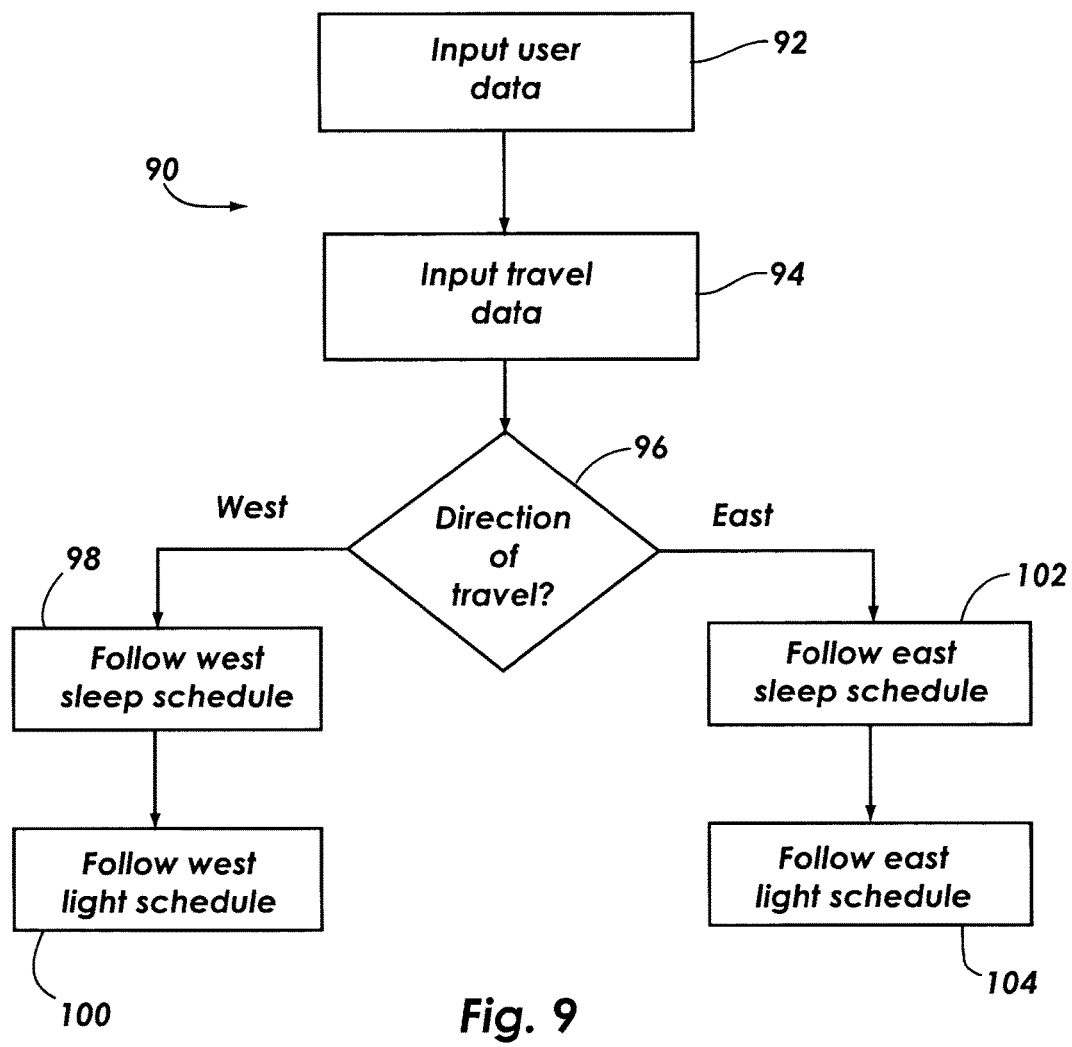
FIG. 9 is a flow diagram showing one implementation of the light delivery method.

Looking now at FIG. 9, a flow diagram 90 is shown, describing a process that may be used by the processor 20, shown in FIG. 1. The processor 20 may use an algorithm that accepts data input from a user. This data may include user data inputs 92 and travel data 94.

The software utilized by the processor 20 could be embedded in the processor 20 or could be downloaded by processor 20 from the internet or other external source, as needed.

Examples of data that is input to the processor 20 may include the departure airport, arrival airport, natural sleep time and natural wake time. It is known that, in order to achieve the best adjustments in the circadian rhythm, light should be administered relative to the time when the core body temperature is at a minimum. It is also known that, typically, the core body temperature minimum occurs about two hours before the natural wake up time.

The time to expose a subject to light also depends on whether the subject is traveling east-bound or west-bound. If the subject is eastbound, the circadian rhythm adjustment is best made if light is administered after the time when the core body temperature is at a minimum. If the subject is westbound, the circadian rhythm adjustment is best made if light is administered before the time when the core body temperature is at a minimum.

Accordingly, the data to the processor may include the number of time zones traveled, the direction of travel, and the core-body temperature of the traveler. The process then determines at step 96 whether the traveler is headed east or west. It then uses either west-bound sleep and light schedules 98 and 100 or east-bound sleep and light schedules 102 and 104 to calculates a sleep/wake, light/dark regimen and instructions to facilitate the avoidance of jet lag problems. The digital display of the device provides function and text displays to provide the results of the jet-lag calculations.

The data input regarding a subject may also include data regarding whether the subject is "sleep delayed" or "sleep advanced." A sleep delayed subject tends to stay up later and have a more difficult time awakening in the morning, whereas a sleep advanced subject tends to want to go to bed earlier and get up earlier. This data could require separate west-bound and east-bound schedules, depending whether the subject was sleep delayed or sleep advanced.

In one implementation of the light therapy method, the user input is the natural wake up time and the natural fall-asleep time. From this data the processor calculates the time at which the core body temperature is expected to be at a minimum. The user then inputs the departure airport and the arrival airport. The processor calculates the number of time zones to travel and the direction of travel. The process then displays the regimen to follow for each day in order to administer the proper amount of high intensity light for a desired period of time and at the right time. Suggestions may also be given regarding when to go to bed and when to wake up.

The following is an example of implementing the above procedure:

User inputs:
   Natural wake time=7:00 am
   Natural fall-asleep time=11:00 pm
Processor calculates:
   Time at which the core body temperature is at a minimum=5:00 am
User inputs:
   Departure Airport=Washington, D.C.
   Arrival Airport=Paris, France
Processor calculates:
   Number of time zones to travel=6
   Direction of travel=East
   Number of days needed to shift sleep pattern=3

Processor displays:
First day regimen=6 am (East coast time) receive 10,000 lux light exposure,
0.5 hrs. (day before departure).
Second day regimen=4 am (East coast time) receive 10,000 lux light exposure, 0.5 hrs. (departure day).
Third day regimen=8 am (Paris time) 10,000 lux light exposure, 0.5 hrs. (day of arrival)

In addition, the present device can take into account the time when the traveler decides to start making adjustments to the circadian rhythm relative to the time that he begins traveling. For example, a traveler may prefer or be unable to start adjusting the circadian rhythm until arriving at his destination. In such case, the regimen required for making the circadian rhythm adjustment would be considerably different than if the adjust began before the day of travel. The processor in the current device can take the selected start time into account and make the appropriate adjustments in the calculations.

The foregoing discussion deals, by example only, with jet lag travel problems requiring circadian rhythm adjustments. Other types of circadian rhythm disorders or problems may also be effectively treated with the current light therapy device using appropriate data inputs and calculations. Further, the light therapy device may also be useful in treating other types of mood and sleep disorders that are usually responsive to light therapy, including but not limited to seasonal affective disorder, general depression, sleep disorders, and shift-work disorders, post- and ante-partum depression, pre-menstral syndrome, late luteal phase dysphoric disorder (LLPDD), bulimia and eating disorders, and chronic fatigue.

Although the above embodiments are representative of the present invention, other embodiments will be apparent to those skilled in the art from a consideration of this specification and the appended claims, or from a practice of the embodiments of the disclosed invention. It is intended that the specification and embodiments therein be considered as exemplary only, with the present invention being defined by the claims and their equivalents.

What is claimed is:

1. A hand-held apparatus for treating disorders responsive to ocular light therapy, the apparatus comprising:
   a power supply;
   an inverter coupled to the power supply, the power supply being configured to supply power to the inverter;
   a light output device coupled to the inverter to receive power, the light output device including a light emission area, a plurality of cold cathode fluorescent lamp (CCFL) tubes extending along one another over a length parallel to each other with each extending lengthwise in only one direction from one end of the light emission area across to an opposing end of the light emission area, and a reflector formed as a plurality of parabolic reflector portions that are configured to reflect light emitted by the plurality of CCFL tubes in a same emission direction out of a front of the apparatus to illuminate eyes of a subject, the CCFL tubes extending widthwise towards the front beyond a frontal extension of the reflector;
   a processor attached to a backside of a circuit board and coupled through the circuit board to the inverter, the inverter being attached to the backside of the circuit board, the processor configured to control an intensity of the light emitted by the plurality of CCFL tubes in response to an input at least in a form of a user actuation, the processor in response providing an output to the inverter to control a superposition of a pulse width modulated frequency over a current frequency provided to the inverter, the circuit board having a frontside opposing the backside, wherein the reflector rests on and is attached to the frontside of the circuit board; and
   a housing having dimensions of a hand-held device, the power supply, processor, circuit board and the light output device being contained within the housing.

2. The apparatus of claim 1, wherein the power supply is a rechargeable battery, the apparatus comprising a recharger coupled to the rechargeable battery and configured to be coupled to an AC outlet.

3. The apparatus of claim 1, wherein the plurality of CCFL tubes are spaced apart from each other and are together configured to emit a selected spectrum of visible light with a light emission selectively provided at any one of 2,500 lux, 5,000 lux and 10,000 lux at a distance of 6 to 12 inches.

4. The apparatus of claim 3, wherein each one of the plurality of parabolic reflector portions extend lengthwise in the one direction from the one end of the light emission area across to the opposing end of the light emission area and have a focal point positioned at a respective one of the plurality of CCFL tubes to enhance the illumination.

5. The apparatus of claim 1, wherein each of the plurality of CCFL tubes is disposed at a focal point of the respective parabolic reflector portion.

6. The apparatus of claim 3, wherein the power supply is a portable rechargeable battery.

7. The apparatus of claim 1, comprising a lens disposed between the plurality of CCFL tubes and the subject, the lens being textured to diffuse the emitted light.

8. The apparatus of claim 4, wherein the power supply is a portable rechargeable battery.

9. The apparatus of claim 1, wherein the power supply is integral with the apparatus.

10. The apparatus of claim 1, wherein the inverter is configured to produce the pulse width modulated frequency thereby producing a dimming function of the plurality of CCFL tubes.

11. The apparatus of claim 10, further comprising a display coupled to the processor, the processor being configured to display information on the display.

12. The apparatus of claim 10, wherein the data input comprises two or more data input buttons coupled to the processor to provide data to the processor through the input identifying a user natural sleep time and a user natural wake time.

13. The apparatus of claim 1, wherein the inverter is configured to provide a dimmer and a ramp function at the inverter to modulate the amount of power from the inverter to the light source.

14. The apparatus of claim 1, further comprising a manual timer connected to the power supply for manually selecting a period of treatment.

15. The apparatus of claim 1, wherein the emitted light comprises the full visible spectrum of light.

16. The apparatus of claim 1, wherein the emitted light comprises a selected range of wavelengths.

17. A hand-held device for treating disorders responsive to ocular light therapy, the apparatus comprising:
   a light source configured to emit light suitable for ocular light therapy, the light source including a plurality of cold cathode fluorescent lamp (CCFL) tubes extending lengthwise along one another over a length oriented parallel to one another and a reflector formed as a plurality of parabolic reflector portions that are configured to reflect light emitted by the plurality of CCFL tubes out of a front of the device, the CCFL tubes extending widthwise towards the front beyond a frontal extension of the reflector;

an inverter coupled to a power supply and the light source to provide power to the light source;

a processor attached to a backside of a circuit board and coupled through the circuit board to the inverter, the inverter being attached to the backside of the circuit board, the processor configured to control an intensity of the light emitted by the plurality of CCFL tubes in response to an input at least in a form of a user actuation, the processor in response providing an output to the inverter to control a superposition of a pulse width modulated frequency over a current frequency provided to the inverter, the circuit board having a frontside opposing the backside, wherein the reflector rests on and is attached to the frontside of the circuit board; and a hand-held sized housing having an aperture in an interior portion including the power supply, processor, circuit board and the light source, the plurality of CCFL tubes being positioned in the aperture.

18. The device of claim 17, wherein corresponding ones of the plurality of parabolic reflector portions are positioned adjacent to and extend lengthwise along each of the plurality of CCFL tubes from one end of a light emission area across to an opposing end of the light emission area to reflect the light of the plurality of CCFL tubes towards the eyes of the subject.

19. The device of claim 18, wherein each CCFL tube is disposed at a focal point of the corresponding one of the plurality of parabolic reflector portions.

20. The apparatus of claim 1, further comprising a lens disposed between the plurality of CCFL tubes and the subject, the lens being textured to diffuse the emitted light.

21. The apparatus of claim 4, wherein the light output device comprises: a textured lens through which the emitted light passes.

22. The apparatus of claim 1, wherein the processor is configured to calculate a period of time of the emission of light.

23. The apparatus of claim 1, wherein the processor is configured to calculate a time of day or night of the emission of light.

24. The apparatus of claim 1, further comprising a display unit in communication with the processor, the processor configured to display on the display unit information regarding the amount and timing of the emission of light.

25. The apparatus of claim 1, wherein the processor is configured to calculate an amount and timing of the emission of light.

26. The apparatus of claim 25, wherein the inverter is configured to reduce or increase the emission of light to simulate decreasing light at dusk or increasing light at dawn, respectively.

27. The apparatus of claim 1, wherein the data input device comprises buttons coupled to the processor.

28. The apparatus of claim 27, wherein the processor is configured to receive data via the input regarding the subject and the processor is configured to calculate at least one of an amount and a timing of the emission of light to be delivered by the light output device based on the data regarding the subject.

29. The apparatus of claim 27, wherein the processor is configured to receive data via the input regarding travel already taken or yet to be taken by the subject and the processor is configured to calculate at least one of an amount and a timing of the emission of light to be delivered by the light output device based on the data regarding travel already taken or yet to be taken.

30. The apparatus of claim 1, further comprising a cover pivotally coupled to the housing and configured to pivot from a first position covering the light output device to a second position, wherein the second position the cover extends outward perpendicular to the housing to support the housing upright on a surface with the cover extending parallel to and along the surface.

31. The apparatus of claim 7, further comprising a cover pivotally coupled to the housing and configured to pivot from a first position covering and extending parallel to the lens, to a second position wherein the cover extends outward perpendicular to the housing to support the housing upright on a surface with the cover extending parallel to and along the surface.

* * * * *